United States Patent
Nicholas (10) Patent No.: US 6,945,995 B2
(45) Date of Patent: Sep. 20, 2005

(54) STENT OVERLAP POINT MARKERS

(75) Inventor: Peter M. Nicholas, Boston, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 10/231,374

(22) Filed: Aug. 29, 2002

(65) Prior Publication Data

US 2004/0044398 A1 Mar. 4, 2004

(51) Int. Cl.⁷ .................................................. A61F 2/06
(52) U.S. Cl. ..................................... 623/1.34; 623/1.15
(58) Field of Search ............................... 633/1.11–1.34

(56) References Cited

U.S. PATENT DOCUMENTS

| | | | | | |
|---|---|---|---|---|---|
| 4,580,568 | A | * | 4/1986 | Gianturco | 606/198 |
| 5,591,230 | A | * | 1/1997 | Horn et al. | 623/1.17 |
| 5,718,724 | A | * | 2/1998 | Goicoechea et al. | 606/194 |
| 5,725,572 | A | * | 3/1998 | Lam et al. | 623/1.16 |
| 5,954,743 | A | | 9/1999 | Jang | 606/198 |
| 6,051,020 | A | | 4/2000 | Goicoechea et al. | 623/1 |
| 6,117,167 | A | | 9/2000 | Goicoechea et al. | 623/1.16 |
| 6,203,568 | B1 | * | 3/2001 | Lombardi et al. | 623/1.13 |
| 6,258,117 | B1 | * | 7/2001 | Camrud et al. | 623/1.16 |
| 6,312,456 | B1 | * | 11/2001 | Kranz et al. | 623/1.13 |
| 6,315,794 | B1 | * | 11/2001 | Richter | 623/1.34 |
| 6,340,368 | B1 | * | 1/2002 | Verbeck | 623/1.34 |
| 6,344,053 | B1 | * | 2/2002 | Boneau | 623/1.11 |
| 6,402,777 | B1 | | 6/2002 | Globerman et al. | 623/1.11 |
| 6,503,271 | B2 | * | 1/2003 | Duerig et al. | 623/1.15 |
| 6,579,310 | B1 | * | 6/2003 | Cox et al. | 623/1.16 |
| 6,623,521 | B2 | * | 9/2003 | Steinke et al. | 623/1.16 |
| 2002/0052648 | A1 | | 5/2002 | McGurkin | 623/1.35 |
| 2003/0028241 | A1 | * | 2/2003 | Stinson | 623/1.15 |
| 2003/0121148 | A1 | * | 7/2003 | DeCaprio | 623/1.34 |
| 2003/0139799 | A1 | * | 7/2003 | Ley et al. | 623/1.15 |
| 2003/0149473 | A1 | * | 8/2003 | Chouinard et al. | 623/1.15 |
| 2003/0181968 | A1 | * | 9/2003 | Xie et al. | 623/1.13 |
| 2003/0204245 | A1 | * | 10/2003 | Brightbill | 623/1.16 |

OTHER PUBLICATIONS

U.S. Appl. No. 10/084,766, filed Feb. 26, 2002, Brucker et al.
U.S. Appl. No. 10/083,711, filed Feb. 26, 2002, Brucker et al.
U.S. Appl. No. 10/083,707, filed Feb. 26, 2002, Brucker et al.

* cited by examiner

Primary Examiner—Suzette J-J Gherbi
(74) Attorney, Agent, or Firm—Vidas, Arrett & Steinkraus (57) ABSTRACT

A medical device and method of providing same, comprises a first stent body and a second stent body wherein the medical device is formed when the at least one first marker portion and the at least one second marker portion of the stent bodies are positioned in a predetermined alignment wherein the first stent body and the second stent body are aligned along substantially the same longitudinal axis and at least a portion of the first end region and at least a portion of the second end region of the respective stent bodies are overlappingly arranged to provide the medical device with a longitudinal length that is less than the sum of the first stent body length and the second stent body length.

23 Claims, 9 Drawing Sheets

STENT OVERLAP POINT MARKERS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable.

Balloon expandable stents are typically disposed about a balloon which must be positioned and inflated to expand the stent radially outward. Self-expanding stents expand into place when unconstrained, without requiring assistance from a balloon. Some stents may be characterized as hybrid stents which have some characteristics of both self-expandable and balloon expandable stents.

Typically, a stent or other endoluminal prosthesis is implanted in a vessel at the site of a stenosis or aneurysm by so-called "minimally invasive techniques" in which the stent is compressed radially inwards and is delivered by a catheter to the site where it is required. When the stent is positioned at the correct location, the stent is caused or allowed to expand to a predetermined diameter in the vessel and the catheter is withdrawn.

In the past, stents have been generally tubular but have been composed of many configurations and have been made of many materials, including metals and plastic. Ordinary metals such as stainless steel have been used as have shape memory metals such as Nitinol and the like. Stents have also been made of bio-absorbable plastic materials. Stents have been formed from wire, tube stock, etc. Stents have also been made from sheets of material which are rolled.

In order to better provide for the precise placement of the stent within a body location some stents include radiopaque materials which may be detected through the use of fluoroscopy. In this manner the position of the stent within a body vessel may be identified. Radiopaque materials are well known and have been incorporated into stents in several ways. For example, in U.S. Pat. No. 6,402,777 rivets made of radiopaque material are positioned in stent openings; in U.S. Pat. No. 5,725,572 a stent is said to include a radiopaque material affixed to undeformed components at the distal or proximal end of the stent; and in U.S. Pat. No. 5,954,743 at least partially plating a stent with radiopaque material is described.

Stents are known to have a variety of shapes sizes and structural features. For example, stents may have a variety of lengths, diameters, cell configurations, end effects, etc. Stents may be branched or segmented for use in a vessel bifurcation. Such stents may also include one or more ports or crowns where additional stent bodies may be engaged. Some examples of stents having at least some of the structural features mentioned above are described in the following references: U.S. patent application Ser. No. 10/084,766; U.S. patent application Ser. No. 10/083,707; U.S. patent application Ser. No. 10/083,711.

In some cases it is necessary or desirable to place multiple stents, so that the stents are arranged in an end to end manner within a vessel or other body space. Recent studies have shown that in some cases, such as in some applications of drug coated stents, prevention of restenosis may be improved when the ends of adjacent stents are made to overlap one another according to a predetermined alignment. Currently however, precise multiple stent alignment wherein the overlapping stents have a preferred length of stent end overlap is difficult to achieve.

All US patents and applications and all other published documents referred to anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is embodied in a variety of different forms. For example, some embodiments of the invention are directed to methods and systems for treating a stenosis by implanting at least two stents or stent bodies into a vessel, wherein the stent bodies are placed in an overlapping relationship. In order to provide the resulting stent assembly with stent bodies having a desired overlapping configuration, the respective stent ends are provided with one or more alignment markers that allow the stent end to be overlappingly aligned in a very precise manner. The markers may have a greater or lesser degree of radiopacity than the surrounding end regions. In at least one embodiment the markers and/or other portions of the stent bodies may be MRI compatible.

In the various embodiments of the invention, the manner and degree, or length, of stent overlap may be varied. For example, in some embodiments the overlapping stent bodies are configured such that when they are overlapped, at least a portion of one stent is positioned radially within the lumen defined by another stent. In some embodiments the overlapping stent bodies are configured such that when they are overlapped, the stent bodies are longitudinally adjacent to one another. In at least one embodiment in the region where the longitudinally adjacent stent bodies are overlapped, the diameter of each stent body is substantially the same.

In some embodiments the invention is directed to a bifurcated stent that defines a side opening, crown or branch. The branch may be configured to overlap, or be overlapped by a secondary stent body.

In some embodiments at least a portion of at least one of the stents is drug coated. In at least one embodiment, the end of at least one stent is coated. In at least one embodiment one or more ends of adjacent stents are selectively coated. By selectively coating the ends of adjacent stents, the overlapping ends of the stents may be provided with amounts or concentrations of coating such that overlapping ends of the stent bodies provide a coated interface with the surrounding vessel that is substantially the same as the non-overlapped coated portions of the stent bodies. In at least one embodiment the ends of the stent bodies may be selectively coated to have different proportions of the drug coating relative to the proportion of coating on the remaining portions of the respective stent bodies. In at least one embodiment the proportionally amount of drug coating on the overlapped portion of the stents may be greater than or less than the amount of drug coating elsewhere on the stent bodies.

In at least one embodiment at least a portion of the adjacent ends of the stent bodies are engaged to one another. In at least one embodiment overlap of the ends of the stents is by frictional, mechanical, electromagnetic, chemical, or other engagement. In at least one embodiment the at least one stent end is uniquely keyed to the end of an adjacent stent.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
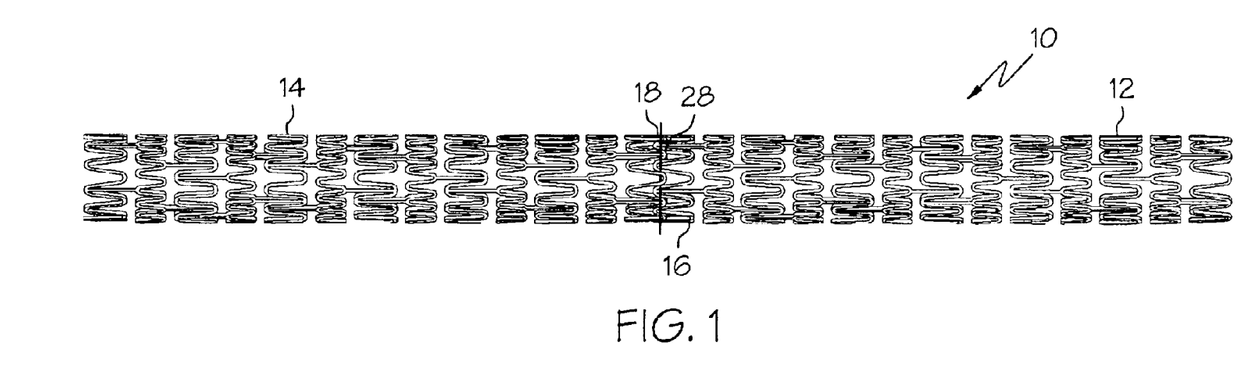
FIG. 1 is a side view of an embodiment of the invention.
Figure 2:
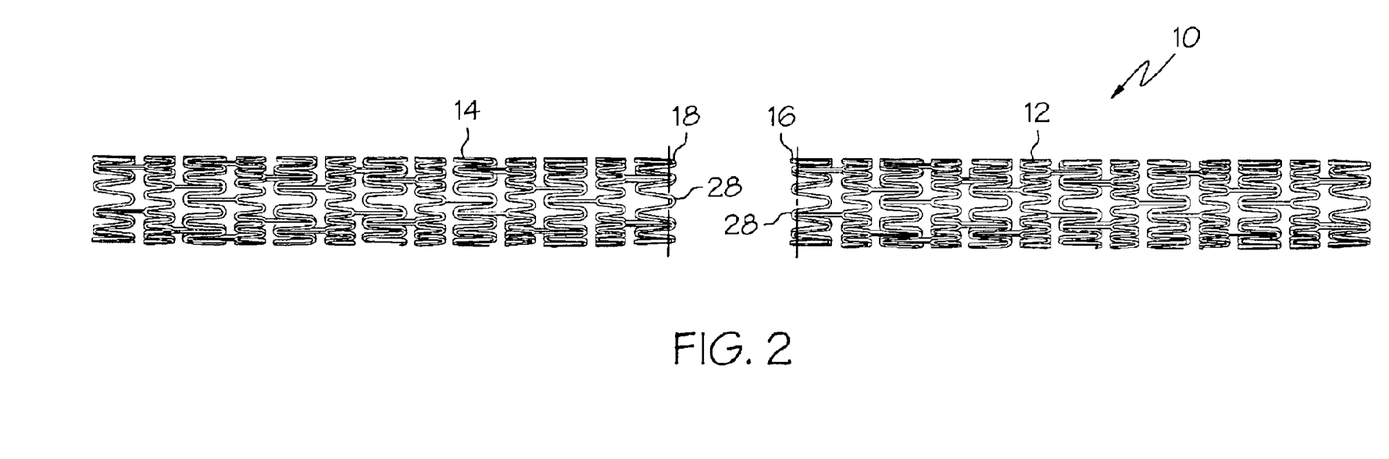
FIG. 2 is a side view of the embodiment shown in FIG. 1 wherein the individual stent bodies are shown separated.

As indicated above, the present invention is directed to a variety of different embodiments. An example of one such embodiment is shown in FIG. 1 wherein a stent assembly, indicated generally at 10, is shown. In various embodiments of the invention stent assembly 10 may be comprised of two or more stents or stent bodies 12 and 14 such as is shown in FIG. 2. Stent bodies may be any sort of implantable prosthesis such as stents, grafts, stent-grafts, vena cava filters, etc.

Stent bodies 12 and 14 may be balloon expandable stents, self-expandable, or hybrid expandable. Stent bodies 12 and 14 may be single layer or multi-layer devices. The bodies may have the same or different construction and expansion characteristics. In some embodiments, one or more of the stent bodies 12 and 14 may be at least partially constructed from a shape memory metal such as nitinol (Ni—Ti), or a shape-memory polymer.

To form stent assembly 10, stent bodies 12 and 14 are positioned together such that at least a portion of their respective end regions 16 and 18 at least partially overlap one another. As indicated above, the manner and degree of end overlap may be varied. For example, in the embodiment shown in FIG. 1, the end regions 16 and 18 of each stent body 12 and 14 have a similar and complimentary configuration which allows at least a portion of the end regions 16 and 18 to interpenetrate one another. Where the stent bodies 12 and 14 are aligned along the same longitudinal axis 15 such as is shown in FIG. 2, the assembly 10 will be provided with substantially the same outer diameter through out its longitudinal length.

Figure 3:
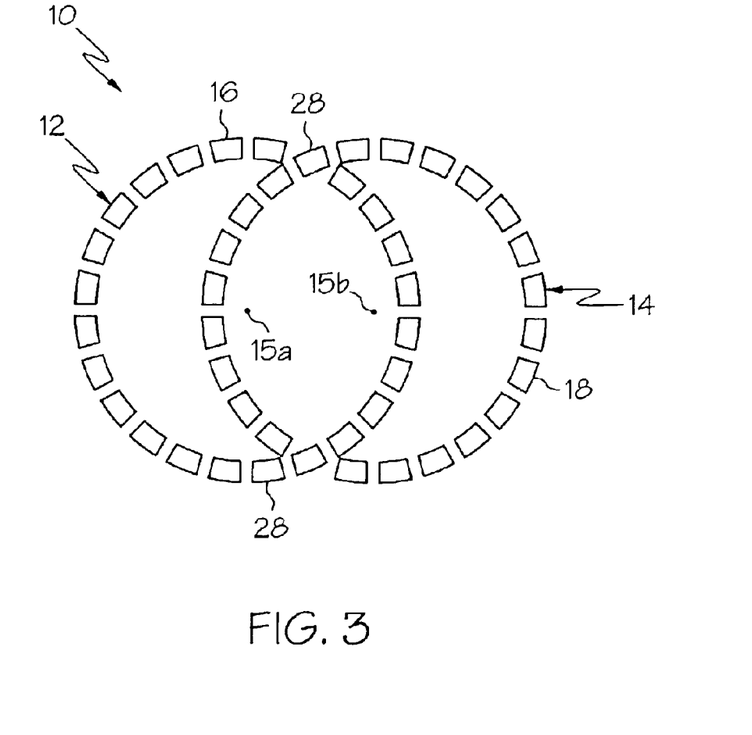
FIG. 3 is a cross-sectional view of an embodiment of the invention.
Figure 4:
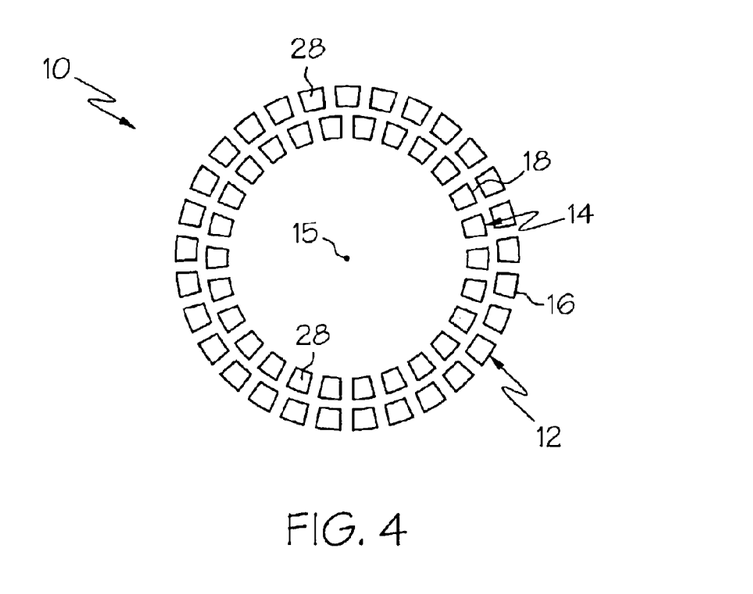
FIG. 4 is a cross-sectional view of an embodiment of the invention.

However, it is recognized that the overlap of end regions 16 and 18 need not always be longitudinally and/or radially aligned. For example, in some cases the stent bodies 16 and 18 may be aligned and overlapped to successfully form assembly 10 even though the stent bodies 16 and 18 have different longitudinal axes, represented as reference numerals 15a and 15b respectively, such as is shown in FIG. 3. In another embodiment illustrated in FIG. 4, end region 18 of stent body 14 may be positioned radially within end region 16 of stent body 12. In the embodiment shown in FIG. 4 the stent bodies 12 and 14 may have substantially the same longitudinal axis 15, but in the portion of the assembly 10 defined by the overlapping end regions 16 an 18 the diameter of stent 12 is less than the diameter of stent 16.

Depending on the particular construction of the stent bodies, other configurations may be possible. Such configurations of overlap made possible by the present invention and are incorporated within its scope.

In order to properly control the alignment and length of overlap of stent bodies 12 and 14, the stents, or portions thereof may include marker portions 28 that allow the end regions 16 and 18 to be visually or otherwise aligned, such as is shown in the various figures.

Markers 28 are preferably constructed from materials that are visually distinct or otherwise detectable. For example, in some embodiments the markers are at least partially constructed from one or more radiopaque materials such as radiopaque metals and/or radiopaque polymers. Though radiopacity is the characteristic that shall be discussed in detail, it should be understood that in some embodiments, markers 28 may be MRI compatible and detectable thereby, X-ray detectable, radio luminescent, may be visually distinct to the naked eye, etc.

In some cases the markers 28 are constructed of radiopaque material to make the markers 28 more visible during fluoroscopy or similar procedures, however in some embodiments, particularly those wherein the end regions 16 and 18 or other portions of the stents 12 and 14 are themselves radiopaque, the markers 28 may be selected to be more or less radiopaque than the surrounding portions of the stents.

The presence of radiopaque markers 28 on the end regions 16 and 18 of the stent bodies 12 and 14, allows the operator or surgeon to position the second stent 14 in relation to the deployed first stent 12 in a precise overlapping alignment configuration, such as any of those described above. The markers located in their respective end regions 16 and 18 may be placed in overlapping alignment or some other recognizable configuration or pattern to ensure proper alignment of the stent bodies 12 and 14. In this manner the markers 28 act as guides to ensure that the proper overlapping arrangement of the end regions 16 and 18 has been achieved.

The extent end regions 16 and 18 are overlapped may depend on a variety of circumstances. For example, where the assembly 10 is utilized in a coronary vessel the length of overlap between the stent end regions 16 and 18 is between about 0.25 mm to about 10 mm, however when the assembly is placed in a peripheral vessel, the overlap may be as great as 20 mm.

The particular material, shape, arrangement, placement, etc. of markers 28 on the end regions 16 and 18 may be any desired. For example, the markers 28 may be at least a portion of one or more individual stent members or be positioned extraneously thereon. The markers may comprise a radiopaque material that is more or less radiopaque than that of the surrounding stent body or bodies 12 and 14. The markers 28 may be an inherent portion of the end regions 16 and 18. Alternatively, the end regions 16 and 18 or portions thereof may be selectively or entirely coated, plated, or otherwise provided with one or more markers 28, such as for example by providing and end region with one or more radiopaque rivets, welds, wires or other structures.

In some embodiments the markers 28 in the completed assembly 10 may be adjacent to one another in a substantially radial, circumferential, longitudinal or other manner. In some embodiments, the markers 28 may be positioned such that markers are spaced apart from one another according to a desired pattern, an example of which being illustrated in FIG. 5. In another embodiment shown in FIG. 6, the markers 28 are intermittently arranged in a pattern about the circumference of the stents 12 and 14, such that when viewed during fluoroscopy the markers 28 appear to form one or more lines, or other patterns. Other configurations and arrangements are possible and are within the scope of this invention.

In the embodiments discussed thus far the formation of assembly 10 is accomplished by deploying the first stent body 12 into the vessel and then subsequently deploying the second stent body 14 in proximity to the first stent body 12 so that the end regions 16 and 18 overlap in the manner desired. In these embodiments however, the alignment of the stents 12 and 14 within the vessel and any frictional engagement that may occur between contacting end regions 16 and 18 may be the primary forces acting to hold the stents together in precise alignment.

In order to more securely engage end regions 16 and 18 together, some embodiments of the invention employ various engagement mechanisms and devices to engage end regions 16 and 18 together. For example, in FIG. 7 the end regions 16 and 18 may be provided with engagement surfaces 22 that provide improved frictional, mechanical, chemical, and/or even electromagnetic interface between the end regions 16 and 18 or portions thereof.

Figure 8:
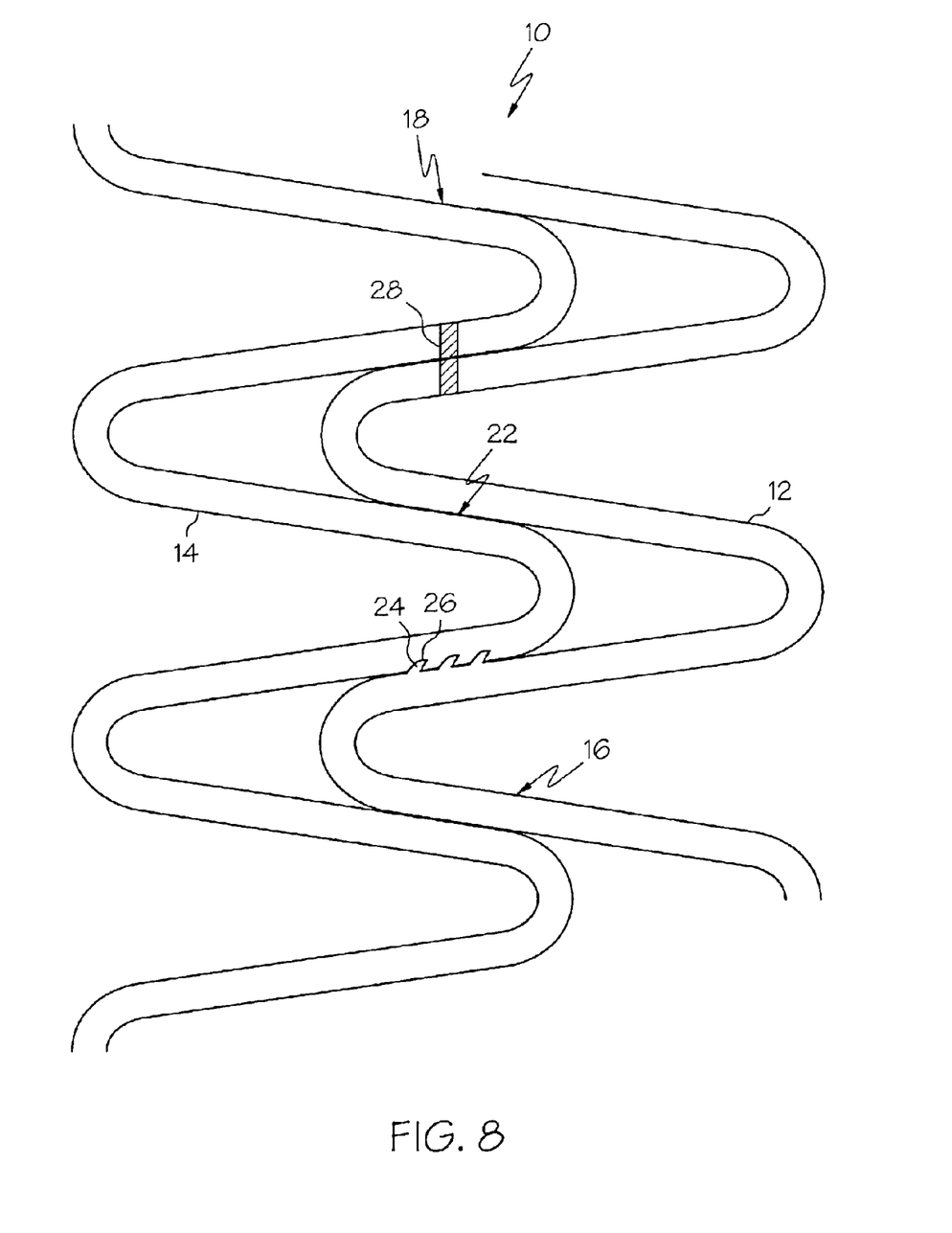
FIG. 8 is a close-up side view of an embodiment of the invention wherein the ends of the assembly are engaged to one another.

An example of one form of engagement surface(s) 22, is illustrated in the embodiment shown in FIG. 8, wherein opposing end regions 16 and 18 are respectively provided with one or more protrusions 24 and receiving surfaces 26. In the embodiment shown, the interface of protrusions 24 and receiving surfaces 26 may provide increased frictional engagement between the regions 16 and 18.

In some embodiments, at least a portion of one or more of the protrusions 24 and/or receiving surfaces 26 may be constructed of a shape memory material allowing the protrusions 24 and/or suifanes 26 to transform to a preset shape upon exposure to an environmental trigger such as a predetenniried temperature, electric current, pH, etc. In this manner the protrusions 24 and/or receiving surfaces 26 may be made to actively and mechanically engage one another for improved securement of the overlapping regions 16 and 18.

In another example, the engagement surfaces 22 may include a coating which adhesively or otherwise aids in chemical engaging the overlapping surfaces together.

In yet another example, at least a portion of the end regions 16 and 18, such as engagement surfaces 22, are provided with opposing magnetic polarity to electromagnetically engage the overlapping surfaces together.

In some embodiments, the stent bodies 12 and 14 or portions thereof, are bioabsorbable to allow the individual stent bodies 12 and 14 to be removed from the body or absorbed thereby at a point in time subsequent to placement of the assembly 10.

Figure 9:
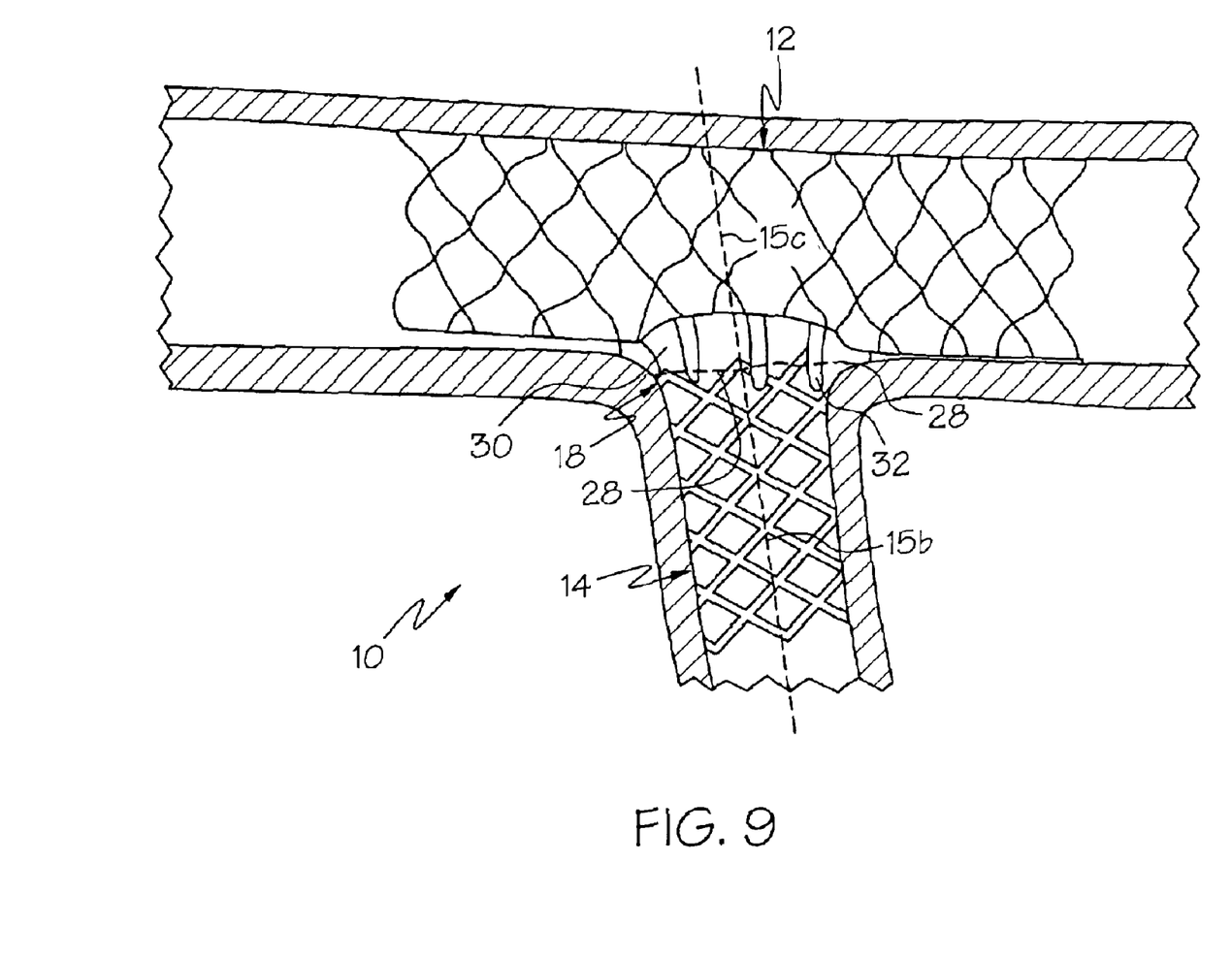
FIG. 9 is a side view of an embodiment of the invention.

As indicated above, some embodiments of the invention are directed to bifurcated stent assemblies, an example of which is shown in FIG. 9. In the embodiment shown a bifurcated assembly, indicated generally at 10, comprises a first stent body 12 and a second stent body 14. First stent body 12 defines a side opening 30. In some embodiments, the side opening 30 may be further defined by a crown or branch 32 of stent material.

In the embodiment shown in FIG. 9 the side opening 30, and/or crown 32 is at least partially defined by one or more markers 28. The second stent body 14 includes an end region 18 which comprises one or more markers 28 as well. In application, after either the first stent body 12 or second stent body 14 is delivered to a bifurcation in a vessel or body lumen, the other body 12 or 14 is positioned adjacent thereto so that at least a portion of the end region 18 of the second stent body 14 and the opening 30 and/or crown 32 of the first stent body 12 are overlapped. The particular configuration of overlap between stent bodies 12 and 14 may include any configuration such as those described above.

Figure 5:
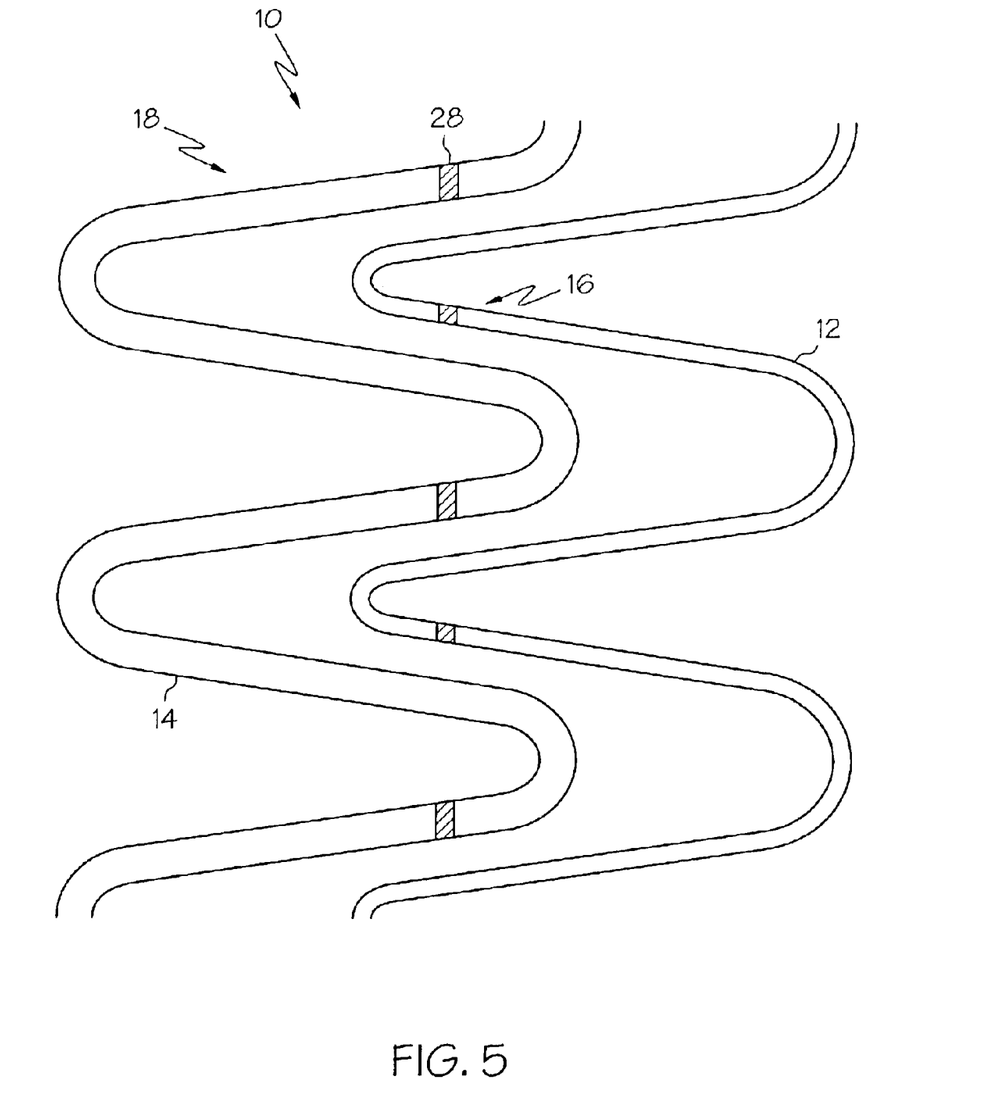
FIG. 5 is a close-up partial side view of an embodiment of the invention illustrating an example alignment of markers.
Figure 6:
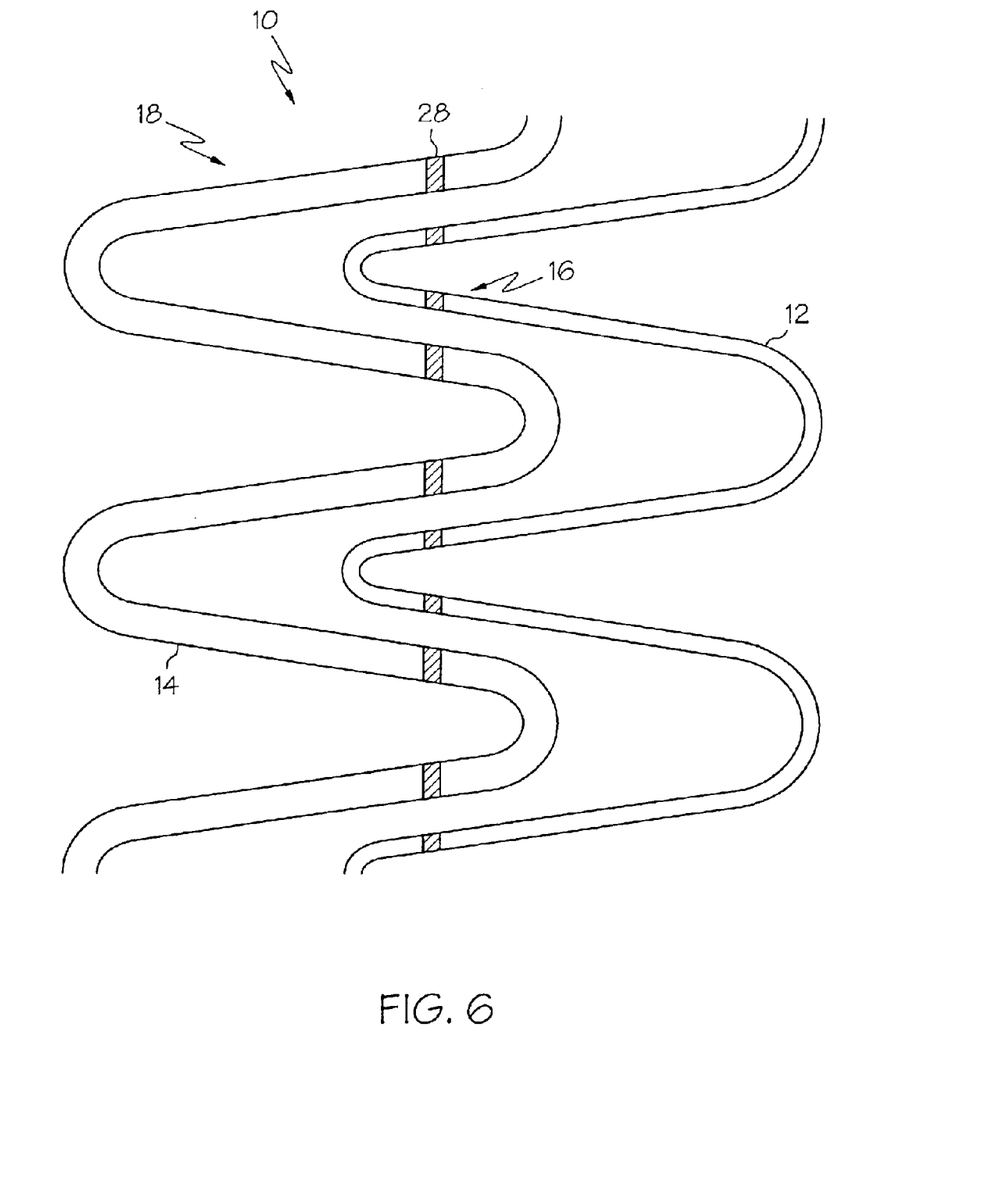
FIG. 6 is a close-up partial side view of an embodiment of the invention illustrating an example alignment of markers.
Figure 7:
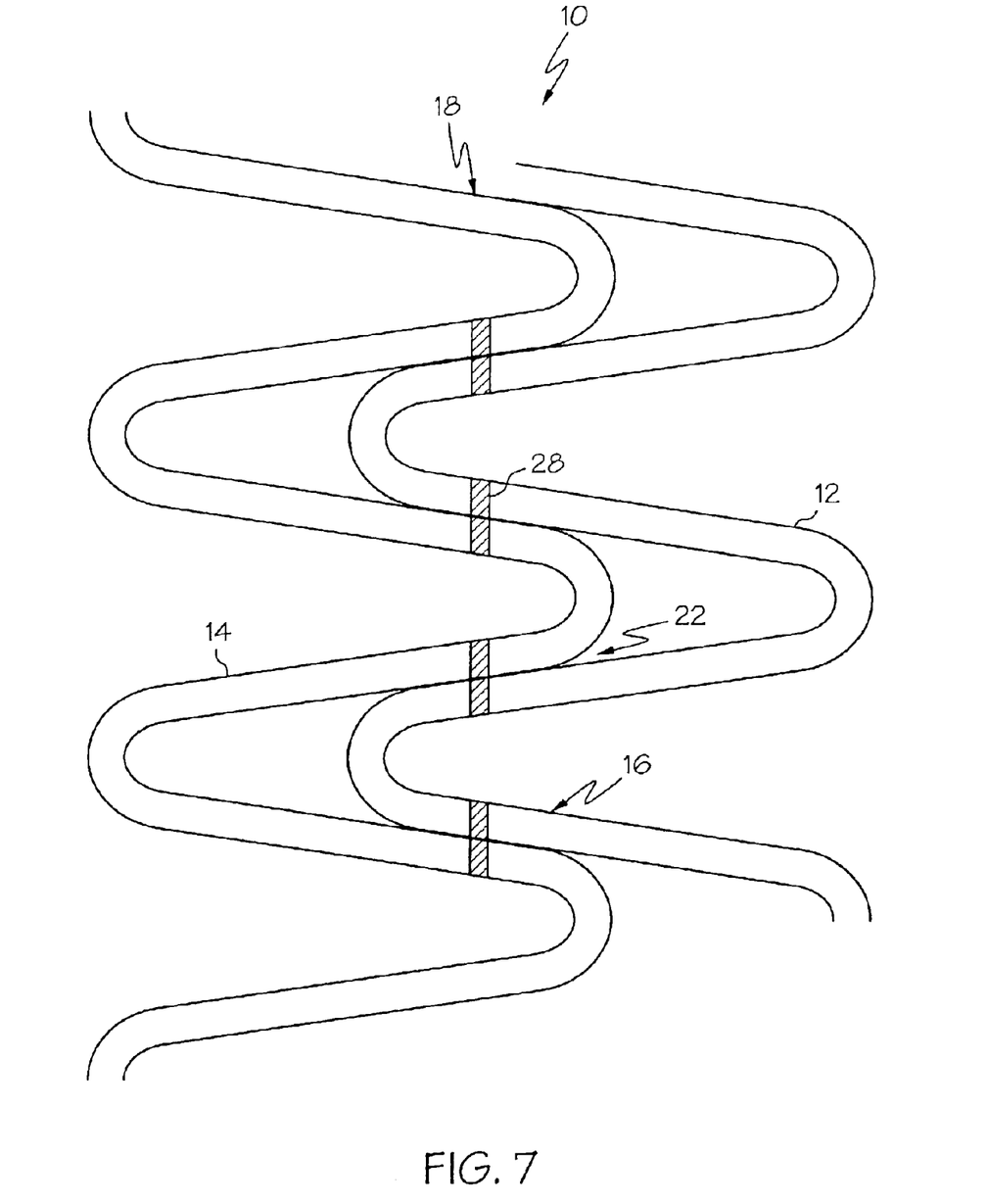
FIG. 7 is a close-up side view of an embodiment of the invention wherein the ends of the assembly are engaged to one another.

When the end region 18 and opening 30 and/or crown 32 are overlapped in a desired configuration, the markers of the respective end region 18 and opening 30 and/or crown 32 will have a predetermined alignment such as is shown in FIGs. 5 and 6. As is shown in FIG. 9, crown 32 defines a longitudinal axis 15c which the longitudinal axis 15b of the second stent body may or may not be aligned with such as in the manners previously described in FIGS. 3 and 4. The overlap of the bodies 12 and 14 forming the completed bifurcated assembly 10 of FIG. 9 may include a physical overlap and/or engagement of the bodies 12 and 14 such as is shown in FIGS. 7 and 8.

In some embodiments, the assembly 10 is at least partially coated with a drug or other substance, the extent that the stent bodies 12 and 14 are coated with a drug or other coating may also affect the manner and degree of the stent overlap.

In some embodiments, particularly those wherein one or more of the stent bodies 12 and 14 are include a drug coating or other drug delivery mechanism, the extent or length of the overlap of the end regions 16 and 18 may be of particular importance.

Figure 10:
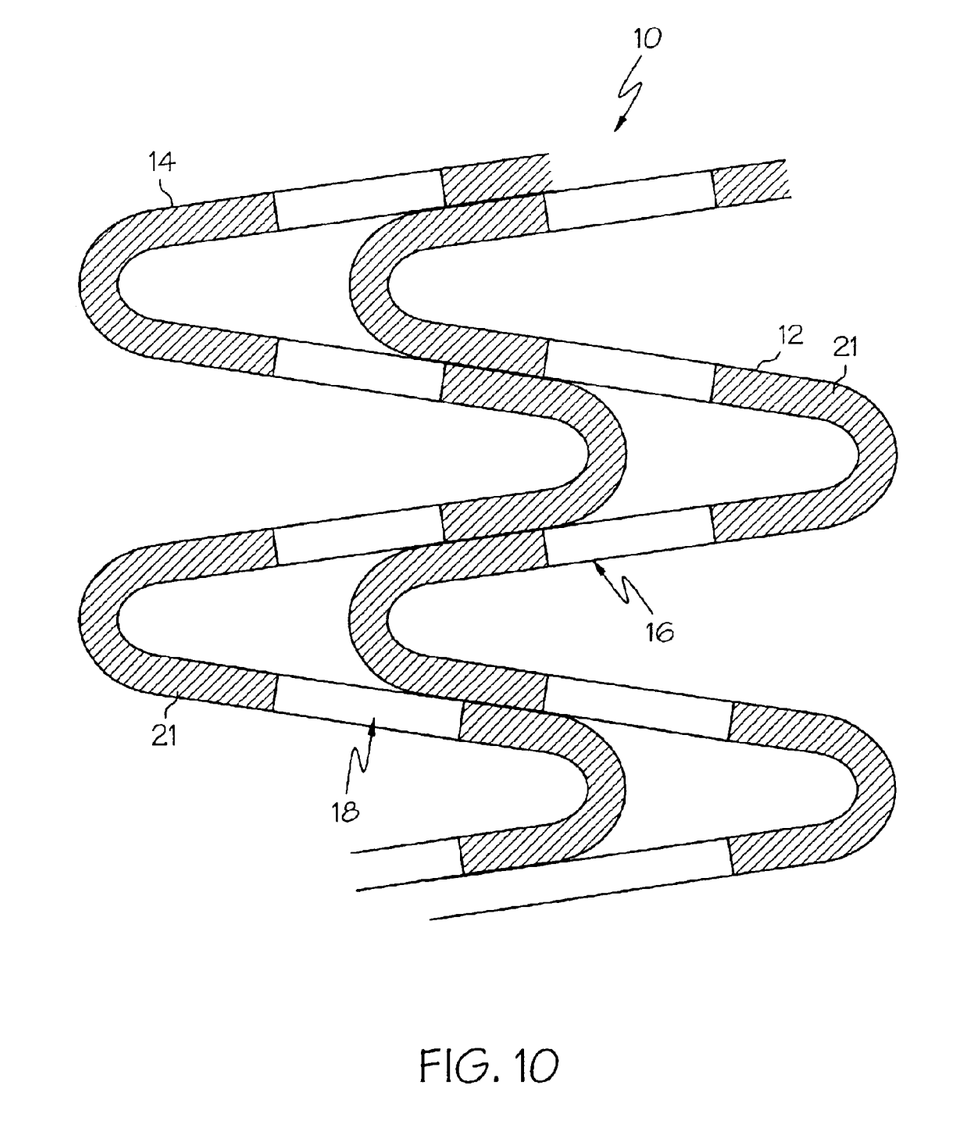
FIG. 10 is a close-up side view of an embodiment of the invention wherein the assembly includes a coating.

Drugs and coatings thereof are well known. The application of such a coating to a stent allows the stent to deliver the drug directly to a desired location within the vessel. However, in many applications it may be of importance to ensure that the concentration, amount, or exposure of the drug along a given length of the stent is substantially consistent. Thus, in some embodiments of the present invention, such as is shown in FIG. 10, the assembly 10 employs a coating 21 of drug that extends across the overlapping end regions 16 and 18. In order to ensure that the exposure of the drug is substantially the same over the length of the assembly, the end regions 16 and 18 are selectively coated to an extent less than adjacent regions of the respective stent bodies 12 and 14, such that when regions 16 and 18 are overlapped to form assembly 10 the exposure of the coating is substantially equal along the entire coated length of the assembly 10.

Figure 11:
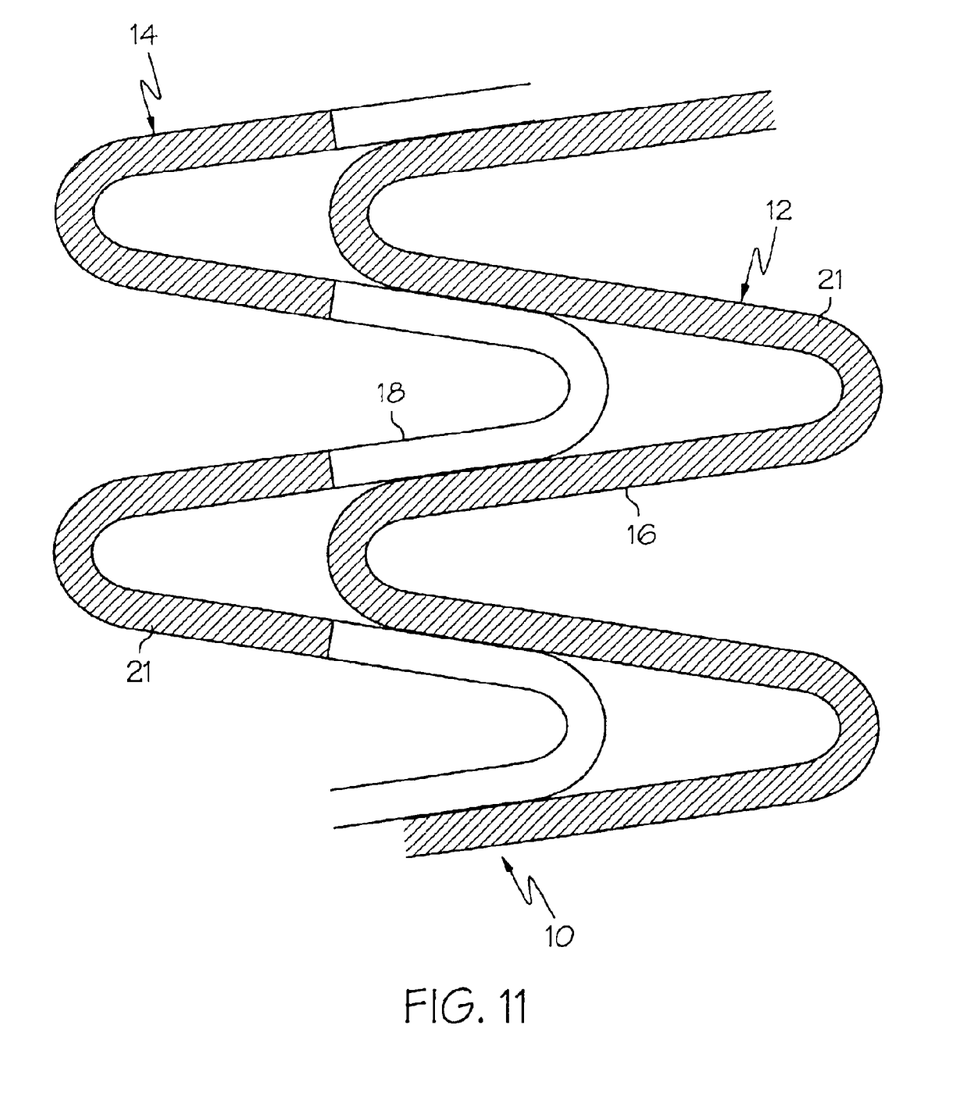
FIG. 11 is a close-up side view of an embodiment of the invention wherein the assembly is includes a coating.

It should be noted, that where a consistent concentration or exposure of a coating is desired, the end regions 16 and 18 need not be selectively coated to an equal proportion. For example, in the embodiment shown in FIG. 11, end region 16 is fully coated (one hundred percent), whereas end region 18 is not at all coated (zero percent). However, the extent of exposure of coating 21 remains substantially constant along the length of the completed assembly 10. In other embodiments, end regions 16 and 18 may be provided with other proportions of coating. In one example for instance, end region 16 may be provided with a 75 percent coating, whereas end region 18 has only 25 percent.

In other embodiments, it may be desired to provide a greater or lesser concentration or exposure of coating 21. In such embodiments, the end regions 16 and 18 may be selectively coated so that when they are overlapped to form assembly 10 the concentration of coating at the overlapped regions 16 and 18 is different than that of the concentration elsewhere along the length of the assembly 10.

In the various embodiments described above, drug coating 21 may be comprised of any or all of a variety of drugs, genetic material, non-genetic therapeutic agents, cells and/or cellular material, polymer coatings, viruses, retro-viruses, and/or other substances. In some embodiments, coating 21 is at least partially radiopaque.

Some particular examples of materials suitable for use as a coating include but are not limited to: anti-thrombogenic agents such as heparin, heparin derivatives, urokinase, PPack (dextrophenylalanine proline arginine chloromethylketone), etc.; anti-proliferative agents such as enoxaprin, angiopeptin, or monoclonal antibodies capable of blocking smooth muscle cell proliferation, hirudin, acetylsalicylic acid, etc.; anti-inflammatory agents such as dexamethasone, prednisolone, corticosterone, budesonide, estrogen, sulfasalazine, mesalamine, etc.; antineoplastic/antiproliferative/anti-miotic agents such as paclitaxel, 5-fluorouracil, cisplatin, vinblastine, vincristine, epothilones, endostatin, angiostatin, thymidine kinase inhibitors, etc.; anesthetic agents such as lidocaine, bupivacaine, ropivacaine, etc.; anti-coagulants such as D-Phe-Pro-Arg chloromethyl keton, an RGD peptide-containing compound, heparin, antithrombin compounds, platelet receptor antagonists, antithrombin anticodies, antiplatelet receptor antibodies, aspirin, prostaglandin inhibitors, platelet inhibitors, tick antiplatelet peptides, etc.; vascular cell growth promotors such as growth factor inhibitors, growth factor receptor antagonists, transcriptional activators, translational promoters, etc.; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, etc.; cholesterol-lowering agents; vasodilating agents; agents which interfere with endogenous vascoactive mechanisms; anti-sense DNA and RNA; DNA coding for anti-sense RNA; DNA coding for tRNA or rRNA to replace defective or deficient endogenous molecules; DNA coding for angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; DNA coding for cell cycle inhibitors including CD inhibitors; DNA coding for thymidine kinase ("TK") and other agents useful for interfering with cell proliferation; DNA coding for the family of bone morphogenic proteins ("BMP's") BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, BMP-16, and dimeric proteins provided as homodimers, heterodimers, or combinations thereof, alone or together with other molecules, as well as other associated proteins; cells or portions thereof of human origin (autologous or allogeneic) or from an animal source (xenogeneic), genetically engineered if desired to deliver proteins of interest at the transplant site; polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.); fibrin; collagen and derivatives thereof; polysaccharides such as celluloses, starches, dextrans, alginates and derivatives; hyaluronic acid; squalene emulsions; polyacrylic acid, such as HYDROPLUS® available from Boston Scientific Corporation, Natick, Mass., and described in U.S. Pat. No. 5,091,205, the entire disclosure of which is hereby incorporated herein by reference; etc.

While the figures included herewith illustrate the relationship between two stent bodies to form the completed assembly, it should be recognized that the inventive assembly and the accompanying method for providing same as described herein may comprise more than two stents or stent bodies overlappingly arranged in similar or different manners.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is

1. A medical device comprising:
   a first stent body, the first stent body defining a first circumferential surface, at least a portion of the first circumferential surface being coated with at least one drug coating, the first stent body having a first stent body length and a first end region, the first end region having a predetermined degree of radiopacity, at least a portion of the first end region having at least one first marker portion, the at least one first marker portion having a predetermined degree of radiopacity different than that of the adjacent first end region, the at least a portion of the first end region having a first magnetic polarity; and
   a second stent body, the second stent body defining a second circumferential surface and the second stent body provided with substantially the same outer diameter as the first stent body along its longitudinal length, at least a portion of the second circumferential surface being coated with the at least one drug coating, the second stent body having a second stent body length and a second end region, the second end region having a predetermined degree of radiopacity, at least a portion of the second end region having at least one second marker portion, the at least one second marker portion having a predetermined degree of radiopacity different than that of the adjacent second end region, the at least a portion of the second end region having a second magnetic polarity, the first magnetic polarity being substantially opposite the second magnetic polarity,
   the medical device being assembled when the at least one first marker portion and the at least one second marker portion are positioned in a predetermined alignment wherein the first stent body and the second stent body are aligned along substantially the same longitudinal axis and the at least a portion of the first end region and the at least a portion of the second end region are overlappingly arranged, and engaged one to the other, to provide the medical device with a longitudinal length that is less than the sum of the first stent body length and the second stent body length, distribution of the at least one drug coating being substantially uniform along the longitudinal length of the assembled medical device, such that concentration of the at least one drug coating is substantially the same where the at least a portion of the first end region and the at least a portion of the second end region are overlappingly arranged as on regions of the first circumferential surface and second circumferential surface adjacent thereto.

2. The medical device of claim 1 wherein the at least a portion of the first end region and the at least a portion of the second end region are chemically engaged.

3. The medical device of claim 2 wherein the at least a portion of the first end region and the at least a portion of the second end region are adhesively engaged.

4. The medical device of claim 1 wherein at least one of the first stent body and second stein body is self-expandable.

5. The medical device of claim 1 wherein at least one of the first stent body and second stent body is at least partially constructed from a shape-memory material.

6. The medical device of claim 1 wherein when the at least a portion of the first end region and the at least a portion of the second end region are overlappingly arranged, the at least one first marker portion and the at least one second marker portion are intermittently arranged about the circumference of the stent.

7. The medical device of claim 1 wherein the first marker portion and the second marker portion have the same degree of radiopacity.

8. The medical device of claim 1 wherein the marker portions are more radiopaque than the surrounding end regions.

9. The medical device of claim 1 wherein the marker portions are less radiopaque than the surrounding end regions.

10. The medical device of claim 1 wherein when the at least a portion of the first end region and the at least a portion of the second end region are overlappingly arranged about 0.25 mm of the first end region overlaps about 0.25 mm of the second region.

11. The medical device of claim 1 wherein when the at least a portion of the first end region and the at least a portion of the second end region are overlappingly arranged at least 0.25 mm of the first end region overlaps at least 0.25 mm of the second region.

12. The medical device of claim 1 wherein when the at least a portion of the first end region and the at least a portion of the second end region are overlappingly arranged up to about 20 mm of the first end region overlaps up to about 20 mm of the second region.

13. A method for providing a multi-stent assembly in a body lumen comprising the steps of:
   advancing a first stent body to a predetermined location in the body lumen, the first intent body defining a first circumferential surface, at least a portion of the first circumferential surface being coated with at least one drug coating, the first stent body having a first stent body length and a first end region, the first end region having a predetermined degree of radiopacity, at least a portion of the first end region having at least one first marker portion, the at least one first marker portion having a predetermined degree of radiopacity different than that of the adjacent first end region, the at least a portion of the first end region having a first magnetic polarity;

delivering the first stent body by expanding the first stent body to an expanded state;

advancing a second stent body to a location in the body lumen longitudinally adjacent to the first stent body, the second stent body defining a second circumferential surface, at least a portion of the second circumferential surface being coated with the at least one drug coating, the second stent body having a second stent body length and a second end region, the second end region having a predetermined degree of radiopacity, at least a portion of the second end region having at least one second marker portion, the at least one second marker portion having a predetermined degree of radiopacity different than that of the adjacent second end region, the at least a portion of the second end region having a second magnetic polarity, wherein the first magnetic polarity is substantially opposite the second magnetic polarity;

aligning the at least one first stent marker and the at least one second stent marker so that the first stent body and the second stent body are aligned along substantially the same longitudinal axis and at least a portion of the first end region and at least a portion of the second end region are overlappingly arranged;

delivering the second stent body by expanding the second stent body to an expanded state, such that when the second stent body and the first stent body are both in their respective expanded states the at least a portion of the first end second and the second end region are engaged and the assembly is provided with a longitudinal length that is less than the sum of the first stent body length and the second stent body length, distribution of the at least one drug coating being substantially uniform along the longitudinal length of the assembly, such that concentration of the at least one drug coating is substantially the same where the at least a portion of the first end region and the at least a portion of the second end region are overlappingly arranged as on regions of the first circumferential surface and second circumferential surface adjacent thereto.

14. The method of claim 13 wherein the assembly has a substantially uniform diameter throughout the longitudinal length.

15. The method of claim 13 wherein the at least a portion of the first end region defines a receiving surface and the at least a portion of the second end region defines at least one protrusion, the at least one protrusion being engaged to the receiving surface.

16. The method of claim 13 wherein the at least a portion of the first end region and the at least a portion o the second end region are chemically engaged.

17. The method of claim 16 wherein the at least a portion of the first end region and the at least a portion of the second end region are adhesively engaged.

18. The method of claim 13 wherein at least one of the first stent body and second stent body is self-expandable.

19. The method of claim 13 wherein at least one of the first stent body and second stent body is at least partially constructed from a shape-memory material.

20. The method of claim 13 wherein when the at least a portion of the first end region and the at least a portion of the second end region are overlappingly arranged, the at least one first marker portion and the at least one second marker portion are intermittently arranged about the circumference of the stent.

21. The method of claim 13 wherein the first marker portion and the second marker portion have the same degree of radiopacity.

22. The method of claim 13 wherein the marker portions are more radiopaque than the surrounding end regions.

23. The method of claim 13 wherein the marker portions are less radiopaque than the surrounding end regions.

* * * * *